United States Patent
Bauer

(10) Patent No.: US 7,302,290 B2
(45) Date of Patent: Nov. 27, 2007

(54) HEART-ACTIVITY MONITORING WITH MULTI-AXIAL AUDIO DETECTION

(75) Inventor: Peter T. Bauer, West Linn, OR (US)

(73) Assignee: Inovise, Medical, Inc., Portland, OR (US)

(*) Notice: Subject to any disclaimer, the term of this patent is extended or adjusted under 35 U.S.C. 154(b) by 577 days.

(21) Appl. No.: 10/912,676

(22) Filed: Aug. 4, 2004

(65) Prior Publication Data

US 2005/0033190 A1    Feb. 10, 2005

Related U.S. Application Data

(60) Provisional application No. 60/492,885, filed on Aug. 6, 2003.

(51) Int. Cl.
  *A61B 5/04* (2006.01)
  *A61B 5/02* (2006.01)

(52) U.S. Cl. ............... 600/513; 600/528; 600/514; 381/67

(58) Field of Classification Search ........... 600/513, 600/514, 528; 381/67
See application file for complete search history.

(56) References Cited

U.S. PATENT DOCUMENTS

| | | | |
|---|---|---|---|
| 4,362,164 A | 12/1982 | Little et al. | |
| 4,528,689 A * | 7/1985 | Katz | 381/67 |
| 4,576,179 A | 3/1986 | Manus et al. | |
| 5,086,776 A | 2/1992 | Fowler, Jr. et al. | |
| 5,685,317 A | 11/1997 | Sjöström | |
| 5,727,549 A | 3/1998 | Suda et al. | |
| 5,813,404 A | 9/1998 | Devlin et al. | |
| 6,050,950 A | 4/2000 | Mohler | |
| 6,757,392 B1 * | 6/2004 | Granzotto et al. | 381/67 |
| 7,110,804 B2 * | 9/2006 | Baumer et al. | 600/372 |
| 7,181,628 B2 * | 2/2007 | Sato et al. | 713/189 |
| 2004/0032957 A1 * | 2/2004 | Mansy et al. | 381/67 |
| 2004/0039420 A1 * | 2/2004 | Jayne et al. | 607/5 |

FOREIGN PATENT DOCUMENTS

WO    WO 88/05282    7/1988

* cited by examiner

*Primary Examiner*—George R. Evanisko
*Assistant Examiner*—Amanda Patton
(74) *Attorney, Agent, or Firm*—Jon M. Dickinson, PC; Robert D. Varitz, PC

(57) ABSTRACT

Apparatus and associated methodology for monitoring correlatable anatomical electrical and sound signals, such as electrical and audio signals produced by human heart activity, including (a) attaching to a selected, common anatomical site ECG (or other) electrode structure, and a multi-axial sound sensor, and (b) simultaneously collecting from adjacent that site both ECG(or other)-electrical and sound signals, where such sound signals arrive adjacent the site along multiple, angularly intersecting axes.

26 Claims, 3 Drawing Sheets

Fig. 7
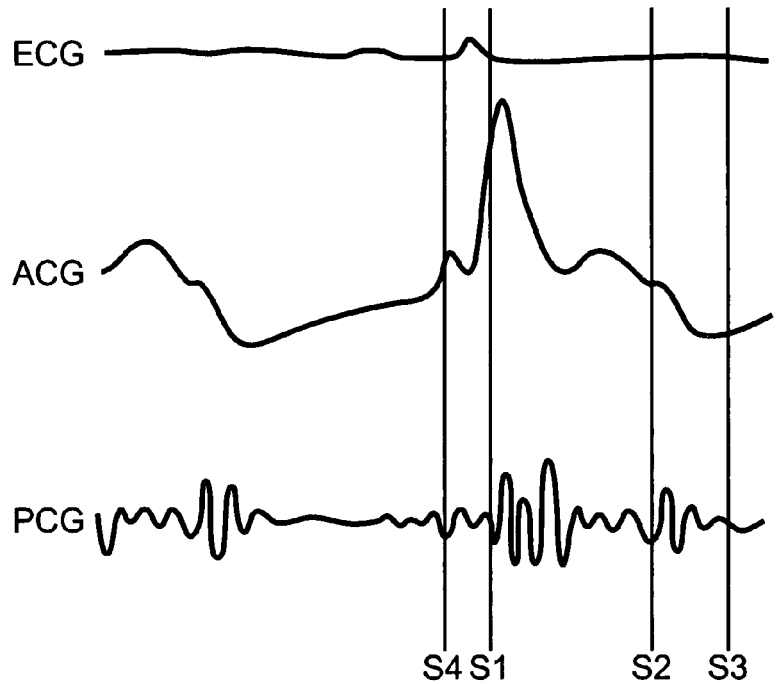
ECG
ACG
PCG
S4 S1    S2 S3
Fig. 8
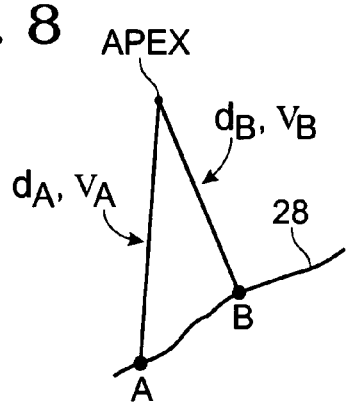
APEX
$d_B, v_B$
$d_A, v_A$
28
B
A
Fig. 9
SHEAR WAVES VELOCITY $\quad v \sim sqrt(\mu/\rho)$
$\mu$: ELASTIC MODULI
$\rho$: DENSITY
⇨ TIME DELAY BETWEEN SENSOR 1 AND SENSOR 2:
$\Delta t \sim sqrt(\rho/\mu)$
⇨ TIME DELAY CAN BE USED TO DETECT CHANGES
IN LUNG/THROAX MATERIAL DENSITY/ELASTICITY

HEART-ACTIVITY MONITORING WITH MULTI-AXIAL AUDIO DETECTION

CROSS-REFERENCE TO RELATED APPLICATION

This application claims priority to U.S. Provisional Patent Application, Ser. No. 60/492,885, filed Aug. 6, 2003 for "Heart-Activity Monitoring With Multi-Axial Audio Detection". The contents of that provisional application are herby incorporated herein by reference.

BACKGROUND AND SUMMARY OF THE INVENTION

This invention pertains to apparatus and methodology associated with the collection of human heart-related anatomical signals—both electrical and audio. It also relates to special signal-collection and signal-output processing. While preferred and best-mode implementations of the invention are referred to throughout herein as involving the heart, it is recognized that other kinds of bio-information may be desirable to collect. Accordingly, reference to the heart in this disclosure should be read and understood to apply to other human anatomy realms.

Prior art collection of ECG-electrical information for diagnostic purposes is very well known. Known also is the fact that collected, heart-activity-produced sound information provides useful diagnostic data. With respect to the matter of sound collection, since the early days of phonocardiography, accelerometers were used to detect heart sounds on the chest wall. All that those accelerometers did was to measure the impulse of sound waves perpendicular to the chest surface. Since the energy of heart vibrations (S1, S2, S3, S4, and murmurs) is transported mostly by shear surface waves, a uni-directional detection apparatus, i.e. a uni-directional accelerometer, will be limited to registering the energy component perpendicular to the surface of the chest wall only.

In one approach to signal collection as proposed by the present invention, both sound (multi-axial) and electrical (ECG) signals are collected simultaneously from a common anatomical site so that ECG signals, and important heart-produced sound signals, such as the S-sound signals known as the S1, S2, S3 and S4 sounds, can be correlated in different ways to produce accurate, useful diagnostic information in a manner which significantly rivals prior art techniques to get at the same information.

Simultaneous, common-site sound and ECG signal collection may be performed selectively with or without axial symmetry, depending upon the physical configuration chosen for signal-collection structure made in accordance with the invention. Attachment to the anatomy, such as to the thorax, may be accomplished in different ways, such as via a suitable bio-gel/adhesive, or by way of a vacuumizing (suction) arrangement.

The proposed signal-collection structure may utilize, selectively, different specific types of ECG electrode structures, with sounds being gathered, as by one or more small accelerometers(s), along three orthogonal (X, Y and Z) axes preferably either by a multi(three)-axis accelerometer, or by three, orthogonally (angularly) oriented, uni-axis accelerometers. The mentioned Z-axis is normal to the surface of the anatomy. Using a multi-axis accelerometer with appropriate sensitivity and load on the chest wall, or correspondingly multiple unidirectional accelerometers with their measurement axes arranged in different orientations to the chest wall, it becomes possible to capture the maximum of the detectable heart sound energy on the surface of the human thorax.

X and Y sound components may be processed and employed: (a) to give certain important X and Y sound analyses that furnish very useful S-sound information; (b) to minimize extraneous noise interference with desired signal information; (c) to give a sense of anatomical surface directionality to guide lateral repositioning of the signal-collection structure so as to maximize the acquisition of Z-axis sound information; and (d) to accomplish other desirable things. Extraneous noise interference can come from many sources, such as from digestive sounds, respiration related sounds, and vibrations due to muscle tension, etc.

With regard to S-sound information, the point of maximum impact (PMI) for vibrations on the chest wall caused by sounds originating in the heart (S1, S2, S3, S4, and murmurs) is classically detected by auscultation. Since many frequency components of the heart sounds, especially the ones related to S3 and S4 heart sounds, are in the inaudible frequency range, and are damped due to absorption of sound energy in human flesh, auscultation results are sometimes inaccurate and simply impossible to perform in certain body positions, especially in the supine position. An additional consideration, addressed by the multi-axial sound collection approach proposed by the present invention, involves the detection of heart sounds in body positions which cannot easily be altered.

In accordance with the invention, direct electrodes/sensors (a) may be integrated or made separable from one to another, (b) may be made reusable or discardable, (c) may carry self-contained internal signal-processing structure, and/or (d) may be made connectable to adapters which carry signal-processing structure. Signal-processing structure, per se, which is employed as generally described herein, is not detailed herein inasmuch as such structure may be constructed in various manners that are well known to those skilled in the art using conventional technology. An on-board electronic memory unit may be provided in a patient-specific-device to capture collected ECG and sound data for future reference. Such a future reference capability can enable serial monitoring of a particular person to furnish valuable risk stratification information.

Appropriate filter circuitry, which may be entirely conventional in construction, may be employed in signal-processing structure to provide what is known as an apexcardiogram output signal.

The many and various features and advantages, including those just mentioned, which are offered by the invention will become more fully apparent as the description which now follows is read in conjunction with the below-described drawings.

DESCRIPTION OF THE DRAWINGS

FIG. 7 is a graph showing relationships between ECG, apexcardiogram and phonocardiogram waveforms.

FIGS. 8 and 9 collaboratively illustrate the use of pairs of ECG electrodes, and multi-axial sound sensors, according to the invention to derive, from ECG-electrical, and sound data, signals traveling over different paths to different sites on the anatomy, certain diagnostically useful heart-activity information.

DETAILED DESCRIPTION OF THE INVENTION

Figure 1:
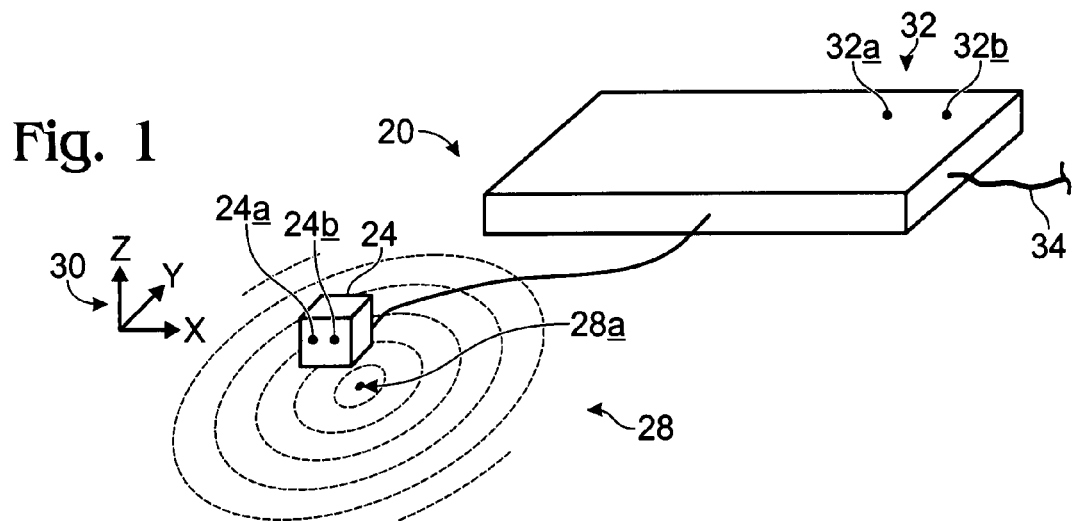
FIG. 1 is a fragmentary, schematic, view illustrating, very generally, heart-activity (anatomical) monitoring structure constructed in accordance with the present invention, and displayed in an operative condition adjacent the surface of a person's chest anatomy.
Figure 2:
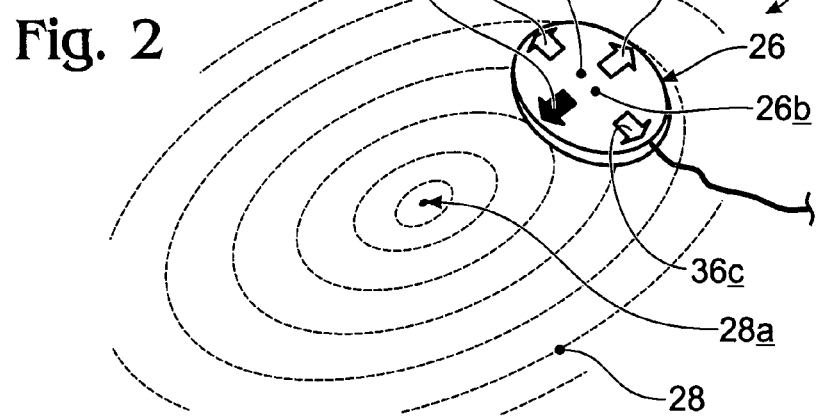
FIG. 2 is similar to FIG. 1, and shows a modified form of the invention.

Turning now to the drawings, and beginning with FIGS. 1 and 2, indicated generally at 20 in FIG. 1, and at 22 in FIG. 2 are two preferred modifications of monitoring structure constructed in accordance with the invention. In each figure, a unitized component containing ECG electrode structure, and a multi-axis sound sensor, are shown schematically by a block 24 in FIG. 1 and by a thin cylindrical disk 26 in FIG. 2. In block 24, the electrode structure and the sound sensor are represented by darkened dots 24a, 24b, respectively. In disk 26, the electrode structure and the sound sensor are represented, respectively, by darkened dots 26a, 26b. The specific constructions of these electrode structures and sound sensors form no part of the present invention, may be quite conventional in construction, and are not detailed herein. Each sound sensor may take the form either of unitary multi-axis device, or a properly oriented plurality, such as three, of individual single-axis devices. Suitable choices for the operating modalities of these sensors, which preferably are formed as MEMS accelerometer devices, include, capacitive, thermal, piezoelectric, and piezoresistive.

Components 24, 26 are shown disposed near, but not yet "attached" (in a step referred to herein as attaching) to the chest surface anatomy 28 of a person, and are intended to detect/collect ECG-electrical, and heart-activity produced sound signals (and especially the well-known S1, S2, S3, S4 S-sound signals and murmurs) simultaneously from a common anatomical site 28a.

Figure 4:
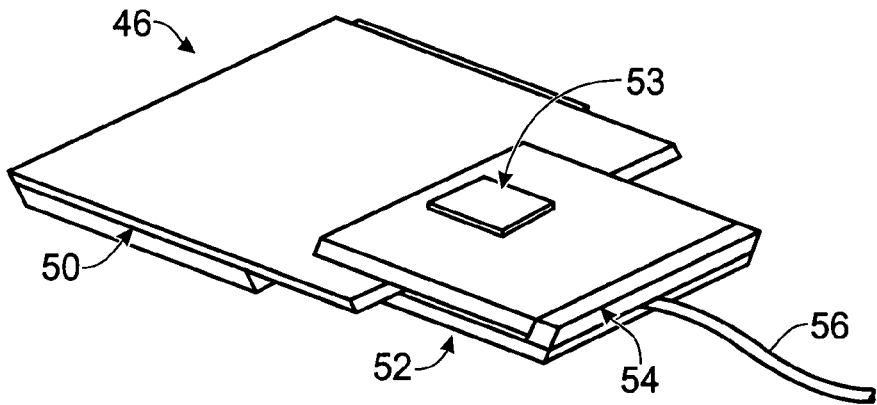
FIG. 4 provides a schematic view of a further modified form of the invention, also illustrating detachability between an electrode structure and an audio sensor which, when attached to one another, and as distinguished from the arrangement shown in FIG. 3, operate "non-coaxially".
Figure 5:
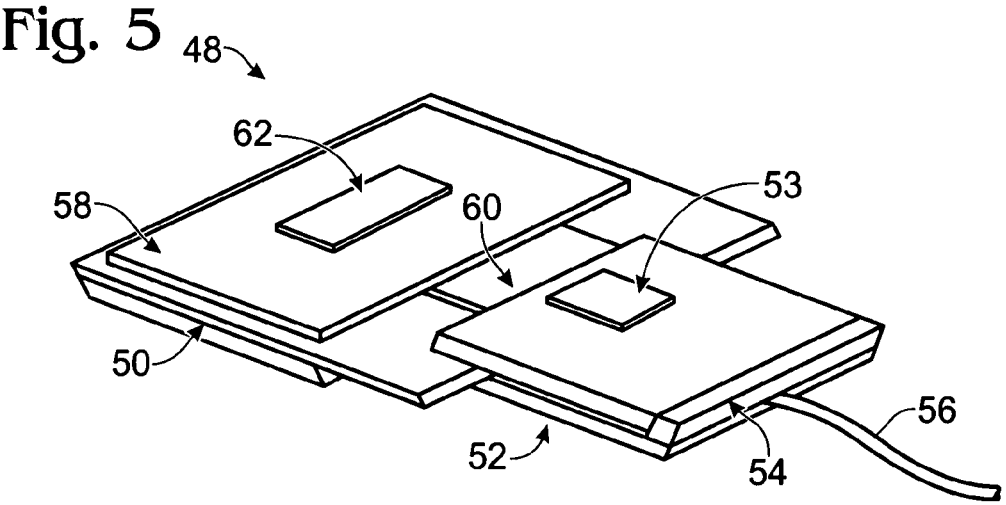
FIG. 5 which is similar to FIG. 4, pictures a version of the structure shown in FIG. 4 including special bio-impedance-matching strip structure.

With respect to sound-signal collection at site 28a, the multi-axis sound sensors are designed according to the invention, to collect such signals arriving at this site simultaneously along multiple, angularly intersecting X, Y, Z axes, shown generally at 30 in FIG. 1. These axes, which are also referred to herein as sound-collecting axes, preferably are at right angles relative to one another, with the Z axis being oriented, during use of the invention, substantially normal to anatomy surface 28a. In components 24, 26, the ECG electrode structure and the sound sensor are appropriately designed to collect their respective signals (Z-axis signal for the sound sensor) along a common axis which is the Z-axis. They could also be designed to collect these same signals along slightly laterally spaced axes. FIGS. 4 and 5, still to be discussed illustrate this practice.

The particular forms of components 24, 26 are reusable and non-patient specific. They could be, if desired however, made to be single-use, patient-specific-only components. In FIGS. 1 and 2, components 24, 26 do not, through they could, carry "on-board" signal processing structure, such as ECG sound signal-processing structure. Rather they are appropriately communicatively "tethered" to outboard signal-processing structure, such as that shown at 32 in FIG. 1 for component 24.

Processing structure 32 includes ECG-electrical signal processing structure 32a and sound-signal processing structure 32b. Structure 32 is connected to suitable output structure which is represented in FIG. 1 as taking the form of an electrical cable 34.

Processed output signals that relate (to each other) simultaneously gathered ECG-electrical and heart-activity-produced sound signals, including what are referred to herein as processed-output apexcardiogram signals, are supplied via cable 34 to suitable external apparatus (not shown). In accordance with practice of the present invention, these processed output signals, and with specific reference now made to sound-reacted signals, may be created in the contest of having used the X and Y components of collected sound information, including appropriate ratios of X and Y signals, to minimize interference from ambient noise signals, and/or to give information, at the time of signal collection, about how to shift the relevant sound sensor laterally on the anatomy so as to collect the maximum available Z-axis sound signal. More will be said shortly regarding this "lateral shifting" consideration.

Referring now especially to FIG. 2, four broad, orthogonally related arrows, 36a, 36b, 36c, 36d are pictured on the side of disk 26 which faces the viewer. These arrows represent lightable indicators which light-up during signal collection to indicate the lateral direction on the anatomy in which component 26 should be shifted in order to collect the largest possible Z-axis sound signal. The signal-processing structure which is associated with the sound sensor in this component utilizes appropriate sound-signal processing, typically in relation to detected X and Y sound signals, to create such anatomical directionality indicators.

Figure 3:
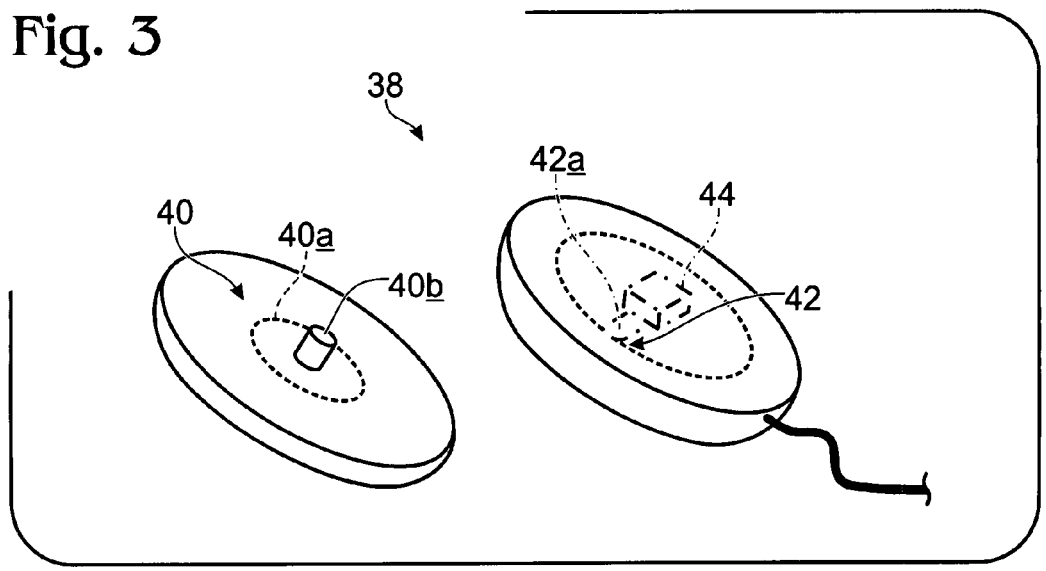
FIG. 3 is a schematic view of yet another modification of the invention illustrating detachability between an electrode structure and an audio sensor which, when attached to one another, operate "coaxially".

Turning attention now to FIG. 3, shown here generally at 38 is another form of monitoring structure constructed in accordance with the present invention. Structure 38 specifically illustrates releasable interconnectivity between two disk-like components 40, 42, where component 40 takes the from of a discardable, patient-specific ECG electrical bio-impedance electrode structure, including an electrode 40a with a connecting pin 40b, and component 42 contains a connecting electrical socket 42a and an embedded, three-axis accelerometer 44 which functions as a sound sensor. Components 40, 42 connect physically and electrically through pin 40b and socket 42a whose specific structures can take a variety of selectable conventional forms. The electrode side of component 40 attaches to the anatomy preferably through an appropriate gel bioadhesive.

While disconnectivity is here shown (in FIG. 3) between the electrode structure and the sound sensor, it should be understood that such electrode structure and sensor may be integrated in a single discardable unit if so desired. FIGS. 4 and 5, next discussed, illustrate this kind of disconnectability.

Directing attention to FIGS. 4 and 5, two quite similar additional modifications of a monitoring structure made in accordance with the invention are shown at 46, 48, respectively. As distinguished from the structure shown in FIG. 3, where mechanical sound pick-up is accomplished on top of electrical electrode structure (on-center, common-axis detection), in FIGS. 4 and 5 sound pick-up is accomplished in an off-center manner—side-by-side with electrical electrode structure. In these two FIGS. (4 and 5) like reference numerals are applied to like structure.

Thus, and describing, first, monitoring structure 46 which has a small-form-factor, thin, rectilinear configuration, this structure includes an electrical signal bioimpedence electrode portion 50 which is coupled mechanically and electrically through a lateral portion 52 containing an embedded, three-axis accelerometer (sound sensor) 53. Structure 46 is disconnectably coupled electrically through an appropriate adapter clip 54 and a cable 56 to out-board signal-processing structure (not shown).

Monitoring structure 48 differs from structure 46 by the inclusion of (a) a thin-layer sound-mass 58, (b) a mechanical coupling bioimpedence layer 60 which couples mass 58 to accelerometer 53, and (c) embedded digital electronic memory structure 62. Mass 58 is suitably designed to respond efficiently to sound energy in the well-known frequency range which characterizes Z-axis heart-produced sounds, and layer 60 functions to couple mechanical energy efficiently from mass 58 to accelerometer 53. Structure 62 functions conventionally under the control of out-board signal-processing structure (not shown) to store collected data for future reference, as mentioned earlier herein.

The exact sizes chosen for components 46, 48, and the various materials employed in their constructions, may be selectable and entirely conventional in nature.

Figure 6:
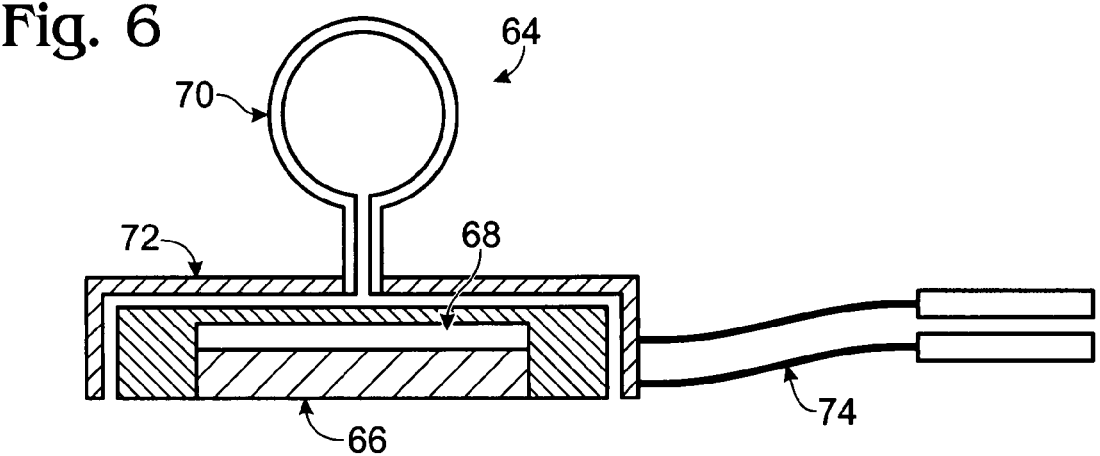
FIG. 6 illustrates schematically still a further modified form of the invention which utilizes a vacuumizing approach to making an attachment to the anatomy.

FIG. 6 illustrates generally at 64 yet another modified form of monitoring structure constructed in accordance with the invention. Unitized within, and associated with, the body of structure 64, are (a) a suitable ECG-electrical electrode and sound collecting structure, generally shown at 66, (b) on-board signal-processing circuitry 68, and (c) a vacuumizing, or suction, system, including a squeeze bulb 70 and fluid-passage structure 72, for using a low-pressure, partial vacuum technique for attaching structure 64 (the lower side as seen in FIG. 6) to the anatomy.

Structure 66 may be constructed with suitable "skin-contacting" (through an electrical bioimpedance gel) conductor structure, and an embedded three-axis accelerometer. Signal-processing circuitry 68 may be constructed to produce substantially all required/desired signal processing of collected electrical and sound signals for delivery to the "outside world" through conductor structure, such as that shown generally at 74.

Signal processing, per se, to achieve useful information with respect to collected ECG-electrical, and sound, signals is relatively straight forward and conventional. The present invention, of course, offers enhanced utility of sound signals by virtue of its collection of multiple (three illustrated) axial sound components.

The presence of X and Y sound components, and particularly the availability of ratios of these components, is especially helpful in minimizing extraneous noise interference, and in helping to detect maximum Z-axis components. Overall, the multi-axis sound-collecting approach proposed by the present invention improves the useful acquisition of the S1, S2, S3 and S4 S-sounds, and murmurs, associated with anatomical heart activity.

For example, to detect a particular S-sound, the electrode/sensor structure of the invention is placed over a site on the anatomy where the point of maximum impact (PMI) for a particular S-sound is expected to occur. From sound data collected at this site, the signal-processing circuitry of the invention looks at the ratio of the X and Y sound components, and at the absolute value of the Z component. If, at that site, the X/Y ratio equals "one", the PMI for that S-sound has indeed been found. If the ratio does not equal "one", then an X/Y ratio calculation can be employed to suggest a direction over the surface of the anatomy in which to move the electrode/sensor structure so as to find the relevant PMI. This process is repeated until maximum PMI is located.

As will be understood by those skilled in the art, X and Y sound components can additionally be employed to detect and characterize shear/surface sound waves for various purposes, such as for the minimizing of extraneous noise interference.

FIG. 7-9, inclusive, relate to the detection, for use and outputting, of a processed apexcardiogram signal. FIG. 7, presented herein for illustrative purposes, graphically illustrates, on a common time base, simultaneously related ECG, apexcardiogram (ACG), and standard phonocardiogram (PCG) wave forms, as well as the "time locations" of the S1, S2, S3 and S4 S-sounds.

FIGS. 8 and 9 self-explanatorily illustrate how pairs of displaced ECG electrodes and sound sensors (devices), made in accordance with the present invention, can be employed to ascertain useful information derived from acquired ECG information and sound data traveling over two different paths. In a more particular sense, this general and very useful capability is illustrated here in the context of obtaining apexcardiogram information. Such paired, two devices (signal-collection units) are illustrated at "A" and "B" in FIG. 8, and are shown placed at laterally spaced locations on the anatomy (28)—locations which reside at different distances $d_A$, $d_B$, respectively, from the apex (labeled APEX) of the heart. The quantities $v_A$ and $v_B$ represent the respective velocities of sound over the two paths leading from the heart apex to the locations of devices "A" and "B", respectively. How to determine these velocities, in a manner well known to those skilled in the art, is described in FIG. 9. In FIG. 9, the term "sqrt" is an acronym for "square root".

From a structural point of view, the invention can be viewed as heart-activity monitor structure adapted to collect, and to deliver as output for assessment, ECG-electrical, and heart-activity-generated sound, signals/data effectively from a selected common anatomical site, with the monitor structure, in operative condition, including ECG electrode structure conductively attachable to a person's anatomy adjacent such a site, and a multi-axial sound sensor unitized with the electrode structure in a manner whereby, with the electrode structure so attached to the anatomy, the sensor is disposed to sense at least heart-activity-generated sounds arriving along multiple, angularly intersecting axes adjacent the selected site.

From one methodological point of view, the invention can be described as including the steps of attaching, to a selected, common anatomical site, ECG electrode structure, and a multi-axial sound sensor, and simultaneously collecting from adjacent that site both ECG-electrical and sound signals, where such sound signals arrive adjacent the site along multiple, angularly intersecting axes.

From another methodologic point of view, the invention can be described as including the steps of establishing at the selected site a mechanical, sound-energy-responsive drive connection between the human anatomy and a multi-axial, motion-to-electrical-signal transducer and collecting multi-axial sounds arriving at that site, and observing multi-axially detected electrical signal components arriving at the selected site, and produced by that transducer in response to anatomy-related, sound-generated motion activities communicated through the established drive connection.

Thus, preferred and various embodiments of the present invention (structure and methodology) have been described and illustrated herein. Notwithstanding this varied-configuration description of the utility, versatility and adaptivity of the invention, other variations and modifications are understood to be possible without departing from the spirit of the invention.

I claim:

1. Heart-activity monitor structure adapted to collect, and to deliver as output for assessment, ECG-electrical, and heart-activity-generated sound, signals/data effectively from a selected common anatomical site, said monitor structure, in operative condition, comprising
ECG electrode structure conductively attachable to a person's anatomy adjacent an anatomical site,
a multi-axial sound sensor unitized with said electrode structure in a manner whereby, with the electrode structure so attached to the anatomy, the sensor is disposed to sense at least heart-activity-generated sounds arriving along multiple, angularly intersecting axes adjacent the selected site, and
sound-signal processing structure operatively connected to said sensor and capable of utilizing X-axis and Y-axis components of detected sound to enable position shifting of the sensor in the vicinity of the site so as to obtain a related maximum Z-axis sound component, wherein said sensor is capable of detecting sounds arriving at such a selected site along orthogonal X, Y and Z axes, where the Z axis is substantially normal to the anatomy at the location of the site.

2. The monitor structure of claim 1, wherein said electrode structure is constructed with selected bio-impedance-matching characteristics.

3. The monitor structure of claim 1 which further includes memory structure operatively connected to said electrode structure and sound sensor for capturing collected data for future reference.

4. The monitor structure of claim 1 which further includes signal processing structure operatively connected to receive and process such output, and to deliver therefrom a processed-output apexcardiogram signal.

5. The monitor structure of claim 1, wherein said electrode structure and said sensor are releasably connectable relative to one another.

6. The monitor structure of claim 1, wherein at least one of said electrode structure and said sensor is non-patient-specific and reusable.

7. The monitor structure of claim 1, wherein said sensor takes the form of multiple uni-axis accelerometers each having respective sound-collecting axes, with each of these sound-collecting axes being differently oriented relative to the other sound-collecting axes.

8. The monitor structure of claim 1, which further includes sound-signal processing structure operatively connected to said sensor and capable of utilizing X-axis and Y-axis components of detected sound to enable the minimizing of sound-signal interference derived from sources including ambient noise and non-heart-related human body sounds.

9. The monitor structure of claim 1, wherein said sensor takes the form of a multi-axis accelerometer.

10. The monitor structure of claim 9, wherein said accelerometer is a MEMS device.

11. The monitor structure of claim 10, wherein said MEMS device operates on a principle featuring, non-exclusively, at least one of capacitive, thermal, piezoelectric, and piezoresistive behavior.

12. Heart-activity monitor structure adapted to collect, and to deliver as output for assessment, at least heart-activity-generated sound signals from a selected anatomical site, said monitor structure comprising
a multi-axial sound sensor effectively attachable to such a selected anatomical site, and when so attached, operable to detect at least heart-activity-generated sounds arriving along multiple angularly intersecting axes located adjacent the selected site, and
output structure operatively connected to said sensor for outputting a signal relating to such detected sounds
wherein said multi-axial sound sensor is constructed and arranged to sense the so-called S1, S2, S3 and S4 sounds (the S-sounds), as well as murmurs, and wherein said multi-axial sound sensor includes signal processing structure operable to evaluate selected X, Y and Z sound-signal ratios in order to determine the point of maximum impact for each of such sounds.

13. The monitor structure of claim 12, wherein said sensor takes the form of a multi-axis accelerometer.

14. The monitor structure of claim 12, wherein said sensor takes the form of multiple uni-axis accelerometers each having respective sound-collecting axes, with each of these sound-collecting axes being differently oriented relative to the other sound-collecting axes.

15. The monitor structure of claim 12 which further includes filter structure responsive to detect sounds to deliver an apexcardiogram output signal.

16. The monitor structure of claim 12, wherein said sensor is capable of detecting sounds arriving at such a selected site along orthogonal X, Y and Z axes, where the Z axis is substantially normal to the anatomy of the location of the site.

17. The monitor structure of claim 16 which further includes plural directional sensors activatable, in relation to X-axis and Y-axis detected sounds, to produce a directional indication of direction on the anatomy toward which to move the sensor so as to maximize the detected Z-axis sound.

18. Methodology for monitoring correlatable ECG-electrical and audio signals produced by human heart activity comprising
attaching to a selected, common anatomical site ECG electrode structure, and a multi-axial sound sensor,
simultaneously collecting from adjacent that site both ECG-electrical and sound signals, where such sound signals arrive adjacent the site along multiple, angularly intersecting axes, and
performing signal processing utilizing collected X-axis and Y-axis sounds to accomplish (a) minimizing extraneous noise interference with desired sound signal information, and (b) offering a sense of anatomical surface directionality to guide lateral repositioning of at least the sound sensor so as to maximize the acquisition of Z-axis sound information.

19. The methodology of claim 18, wherein the axes along which sound signals are collected are X, Y and Z orthogonal axes, with the Z-axis being disposed substantially normal to the anatomy at the selected anatomical site.

20. The method of claim 18, wherein sound-signal collecting by the sound sensor is performed by the use, and stimulation of, a single multi-axis accelerometer.

21. The method of claim 18, wherein sound-signal collecting by the sound sensor is performed by the use, and stimulation of, multiple uni-axis accelerometers.

22. The method of claim 18, wherein said collecting of sound signals includes the collecting, where present, of at least one of the known S-sounds, including S1, S2, S3 and S4, as well as murmurs.

23. The method of claim 18 which further comprises performing signal processing so as to produce a processed-output apexcardiogram signal.

24. A method for monitoring anatomical-activity-produced sounds arriving at a selected anatomical site comprising establishing at the selected site a mechanical, sound-energy-responsive drive connection between the human anatomy and a multi-axial, motion-to-electrical-signal transducer and collecting multi-axial sounds arriving at that site, wherein the sounds are related to heart activity, wherein the axes of sound collection at the site are three in number, and are orthogonally X, Y, Z related to one another, wherein Z-axis sounds are normally oriented relative to the surface of the anatomy at the selected site, and which further includes determining the point of maximum impact of such sounds at that site, and observing multi-axially detected electrical signal components arriving at the selected site and produced by that transducer in response to anatomy-related, sound-generated motion activities communicated through the established drive connection.

25. Methodology for monitoring audio signals produced by human heart activity comprising attaching to a selected, common anatomical site a multi-axial sound sensor, and collecting from adjacent that site sound signals which arrive adjacent the site along multiple, angularly intersecting axes;

processing the sound-signals utilizing X-axis and Y-axis components of a detected sound to enable position shifting of the sensor in the vicinity of the site so as to obtain a related maximum Z-axis sound component, wherein said sensor is capable of detecting sounds arriving at such a selected site along orthogonal X, Y and Z axes, where the Z axis is oriented substantially normal to the anatomy at the location of the site.

26. Heart-activity monitor structure adapted to collect cooperatively, and to deliver as output for assessment, ECG-electrical, and heart-activity-generated sound, signals/data effectively and simultaneously from a pair of selected, laterally spaced anatomical sites, said monitor structure, in operative condition, comprising a pair of signal-collection units, each including (a) ECG electrode structure conductively attachable to a person's anatomy adjacent such a selected site, and (b) an associated, multi-axial sound sensor unitized with said associated electrode structure in a manner whereby, with the electrode structure so attached to the anatomy, the sensor is disposed to sense at least heart-activity-generated sounds arriving along multiple, angularly intersecting axes adjacent the selected site, wherein each of said signal-collection units is constructed and arranged to sense the so-called S1, S2, S3 and S4 sounds (the S-sounds), as well as murmurs, and wherein said multi-axial sound sensor includes signal processing structure operable to evaluate selected X, Y and Z sound-signal ratios in order to determine the point of maximum impact for each of such sounds.

* * * * *